United States Patent [19]

Gabe et al.

[11] Patent Number: 4,640,705
[45] Date of Patent: Feb. 3, 1987

[54] METHOD FOR COMBATTING BLACKGRASS IN CEREAL CROPS AND COMPOSITIONS THEREFOR

[75] Inventors: Julian Gabe, Rehovot, Israel; Richard J. Makepeace, Lower Heyford, United Kingdom

[73] Assignee: Agan Chemical Manufacturers Ltd., Israel

[21] Appl. No.: 511,513

[22] Filed: Jul. 6, 1983

[30] Foreign Application Priority Data

Jul. 7, 1982 [IL] Israel .......................................... 66255
Jul. 21, 1982 [IL] Israel .......................................... 66359

[51] Int. Cl.$^4$ ............................................. A01N 43/70
[52] U.S. Cl. ............................................. 71/93; 71/121
[58] Field of Search ...................................... 71/93, 121

[56] References Cited

FOREIGN PATENT DOCUMENTS 2414870 8/1979 France .
2432833 3/1980 France .

OTHER PUBLICATIONS

Amir et al., Chem. Abst., vol. 85, (1976), 10525HW.
Sarpe et al., Chem. Abst., vol. 93, (1980), 2269p.

Primary Examiner—Catherine L. Mills
Attorney, Agent, or Firm—Ostrolenk, Faber, Gerb & Soffen

[57] ABSTRACT

A method for obtaining satisfactory weed control including control of blackgrass in cereal crops comprising preemergent application of a mixture of terbutryne and trifluralin having a ratio of 1:2 to 2.5:1 and compositions for same, particularly liquid concentrate compositions which do not give crystalline precipitation within 24 hours of emulsification, comprising (a) 7.5 to 18% terbutryne, (b) 15 to 25% trifluralin, (c) 28 to 42% non phytoxic alicyclic ketone, (d) 5 to 15% emulsifier, and (e) stabilizing cosolvent selected from (1) 1 to 3% mesityl oxide, or (2) 8 to 15% lower alkyl esters of C-18 unsaturated fatty acids, or (3) a combination of 10 to 20% isophorone and 1 to 3% di-lower alkyl formamide.

10 Claims, No Drawings

METHOD FOR COMBATTING BLACKGRASS IN CEREAL CROPS AND COMPOSITIONS THEREFOR

The present invention relates to a method for controlling weeds in cereal crops. More specifically, the invention relates to an economical method for achieving wide range weed control in cereals, including control of blackgrass (*Alopecurus myosuroides*) with a selected synergistic combination of terbutryne and trifluralin. The invention also concerns compositions containing mixtures of terbutryne and trifluralin, particularly liquid compositions for use in controlling blackgrass in cereal crops.

Grain fields such as wheat, barley, rye and oats etc, have often presented problems with respect to effective weed control. This is particularly true for grain fields infested with *A. myosuroides* commonly known as blackgrass. This weed is not easily controlled by the generally available herbicides, and those herbicides that do kill the weed are often phytotoxic to the cereal crops as well.

Furthermore, different varieties or species of cereal crops may behave differently to a given herbicide or mixture of herbicides. Thus, some herbicidal compositions may provide quite good weed control and demonstrate a high degree of crop safety in some varieties or species of grain yet cannot be used satisfactorily in other varieties or species. This of course is a big limitation on the utility and versatility of the herbicide.

Another consideration in weed control in general and of grain fields in particular is the great economic and technical advantage of applying herbicides before the emergence of the cultivated plants. The active herbicide is applied immediately after sowing and the weeds are killed even in the germination. This enables unhindered growth of the cultivated plants which leads to considerable increase in the harvest.

For this reason, there has been an ever increasing demand for preemergence herbicides for use in cereal crops which have high selectivity and safety, i.e. the ability to kill undesirable weeds while not injuring or retarding the growth of the crop.

A still further consideration in the use of herbicides is the ease or convenience of application by the farmer. Generally, liquid concentrate formulations are most convenient to use, since these can be readily measured and diluted with water. Particularly convenient to use are single package liquid concentrate formulations which require only dilution with water before spraying.

The herbicide, terbutryne, (2-tert-butylamino-4-ethylamino-6-methylthio-1,3,5-triazine) was disclosed for preemergence use in grain fields in British Pat. No. 1,168,274 and in fact has been commercialized for this purpose. This herbicide is very effective in eliminating the stubborn weed, blackgrass, from cereal crops, including winter wheat. However, it is usable only in fields having a low population of the blackgrass, below 60 flowering heads per square meter because of the low application rate tolerated by the crops. In fields having higher populations of this weed, the results are variable and not sufficiently effective at the recommended rates of 2.8 kg/ha. At higher rates of application, the herbicide can adversely affect the cereal crop itself.

More recent selective herbicides for this particular application, i.e. grain crops, have been claimed, for example, in British Pat. No. 1,255,258. Thus, chlortoluron, (N-4-methyl-3-chlorophenyl N',N'-dimethyl urea), and isoproturon, (N-4-isopropylphenyl-N,N'-dimethyl urea), are considered to be among the better herbicides available today for the control of high populations of blackgrass. These herbicides are rather expensive and there exists a definite need for a more cost effective method of otaining satisfactory and safe weed control in cereal crops.

Trifluralin (2,6-dinitro-N,N-di-n-propyl-4-trifluoromethylaniline) is one of the most successful commercial herbicides to have come unto the market. It was first introduced in the early 1960's and has found ever increasing use in the battle against undesirable weeds. This herbicide has a wide spectrum of activity and is primarily applied as a preemergence herbicide by soil incorporation. It is registered for use in a broad range of crops such as cereal grains, soybeans, cotton, beans, tomatoes, peppers and orchards just to mention a few, and has become a commodity herbicide in terms of tonnage and cost. However, trifluralin is not successful in destroying blackgrass, and it has therefore, not been recommended for this application.

In order to broaden the weed killing spectrum of herbicides, mixtures of different herbicides have been suggested. Thus, trifluralin has been combined with numerous other herbicides to give an array of combinations, many of which show significant synergistic activity.

British Pat. No. 1,213,074 discloses combinations of 2,6-dinitroaniline herbicides (of which trifluralin is the most outstanding example) with halophenoxyalkanoic acids or carboxyl derivatives thereof.

U.S. Pat. No. 3,449,111 discloses a mixture of 2,6-dinitroaniline herbicides and alkyl N,N-dialkyl thiocarbamates.

British Pat. No. 1,460,303 discloses the synergistic combination of 2,6-dinitroaniline herbicides with 3-methylthio-4-amino-6-substituted-1,2,4-triazin-5-ones for use in soybeans.

European Pat. No. 9716 claims synergistic herbicidal compostions for use in cereal crops containing trifluralin and isoproturon.

British Pat. No. 1,248,428 suggests combinations of 2,6-dinitroaniline herbicides with (a) 5-halopyridazones, (b) urea herbicides, (c) s-triazine herbicides, and (d) certain carbamates for protecting crop plants such as cotton, soybean, rape, rice and beets. Terbutryne is not disclosed by this patent. Nor does the patent recommend use of its combination for cereal crops, and certainly not for use against blackgrass.

British Pat. No. 1,473,105 describes specifically formulated liquid herbicidal composition of trifluralin and linuron which is stated to be particularly useful in soil preemergence applications for cereals.

Herbicidal mixtures containing terbutryne as one of the active ingredients are also known. Thus, for example, British Pat. No. 1,251,013 discloses the combinations of terbutryne and nitrofen as useful for controlling weeds in grain crops such as wheat, barley, rye, oats and maize. While this combination may be interesting theoretically, it is not practical since nitrofen has been withdrawn from use for toxicological reasons.

Similarly, French Pat. No. 2,438,970 claims the combinations terbutryne-neburon and terbutryne-nitrofen. The latter is stated to control weeds in winter wheat including *Alopecurus myosuroides.*

British Pat. No. 1,435,694 discloses mixtures of trietazine and terbutryne as selective herbicides and French Pat. No. 2,206,048 claims synergistic combinations of several s-triazines: terbutryne, prometryne and atrazine or simazine.

British Patent Publication No. 2,014,853 discloses the combination of terbutryne with molinate (S-ethyl-N,N-hexamethylene-thiocarbamate) for combatting weeds in cereals, primarily monocotyledons, particularly in winter cereals.

French Patent publications Nos. 2,432,833 and 2,414,870 disclose synergistic three or four component herbicidal compositions based on (1) nitrophenyl halophenyl ethers (2) 2,6-dinitroanilines and/or (3) a urea herbicides and/or (4) s-triazine herbicides. Specifically exemplified are combinations of nitrofen+trifluralin+-terbutryne and trifluralin+linuron+terbutryne. In addition to the problem of toxicity of nitrofen as mentioned above, three component mixtures are more complex to work with and according to the patent, hundreds if not thousands of mixture combinations are possible. None of the mixtures were exemplified against blackgrass and from the large number of possibilities, it is impossible to determine which, if any, 3 way combination would be suitable for this specific application. Furthermore, linuron is rather expensive and makes such a composition too costly.

While numerous combinations of herbicides are known, most of these provide only the combined effect of each individual herbicide and do not exhibit any unusual synergistic effect on the part of the mixture.

Such combinations may be applied separately or as tank mixes or as single package formulations. However, separate application or different herbicides or mixing different herbicidal formulations immediately prior to use are not desirable—because of time, labor and particularly the possibility of error in dosage accuracy and formulation incompatibility. Therefore, single package formulations are most desired.

To this end, special efforts have been made to prepare liquid concentrates from mixtures of herbicides which differ in physical and chemical properties and are thus incompatible in conventionally formulated systems.

For example, in the case of the combination of trifluralin with linuron, which has significant commercial importance, British Pat. No. 1,473,105 mentioned above, proposed the use of acyclic ketones as special solvents to compatibilize the two herbicides in a single formulation. British Patent Publication No. 2,077,104 solved the same problem by using acetophenone as compatibilizing solvent.

French Pat. No. 2,437,786 and its corresponding German Offen. No. 2,900,768 describe a method for preparing water emulsifiable liquid herbicide concentrates from mixtures of active ingredients having different physical-chemical properties, specifically mixtures of (a) dinitroaniline herbicides and (b) triazine herbicides and mixtures of (a) dinitroanilines (b) ureas and (c) s-triazines, by using dialkyl or alkyl formamides e.g. dimethyl formamide, as compatibilizing solvent.

These patents disclose, among others, formulation of a mixture of trifluralin with terbutryne. However, there is no disclosure or suggestion that this combination is particularly effective against blackgrass. In fact, from the little disclosure there is as to utility for the combination, it would appear that it is recommended for use where each of the individual herbicides can be used separately. The invention of these patents resides exclusively in the method of formulating the compounds into a single water emulsifiable liquid composition.

We have discovered that a mixture of terbutryne with trifluralin in ratios of from 1:2 to 2.5:1 and preferably from 1.2:2 to 1:1, when applied preemergence to cereal crops at a rate of 1.0 to 4.5 and preferably 1.5 to 3.5 kg. active ingredients per hectar, gives excellent weed control including control of blackgrass, even at high populations of the weed. This is particularly so in winter varieties of wheat and barley.

Neither of these herbicides alone destroys blackgrass satisfactorily at high population rates, while at the same time avoiding injury to the cereal crops. It is only the combination of these two materials in the specified ratios and application rates that provide satisfactory results.

A further advantage of this particular combination is its wide range of applicability in most varieties of winter wheat and barley. This is not the case with the presently used herbicide chlortoluron, which causes injury to some varieties of cereal crops.

The mechanism of this synergism is not clear, but it appears that the presence of trifluralin increases the effectiveness of smaller quantities of terbutryne in destroying high infestation of blackgrass and also increases the tolerance of cereal crops against injury by terbutryne. In effect, this is a very highly selective herbicide combination for cereal crops in fields with high blackgrass populations. Based on the price structure of herbicides today, the inventive combination offers satisfactory weed control in cereal crops, including blackgrass control, comparable to that provided by chlortoluron, on a much more cost effective basis.

The mixtures of this invention can be applied either separately or together. They can be in the form of wettable powders, solutions, emulsifiable concentrates, flowable concentrates, twin packs or other formulated forms as are common in the industry. Preferably they are applied as a single liquid formulation.

Due to the differences in the physical and chemical properties of terbutryne and trifluralin, these herbicides are not readily formulated into stable liquid concentrates. Specific formulations have, therefore, been developed using special solvents. This is especially the case when one desires liquid concentrate compositions having long term low temperature stability enabling storage of the liquid concentrate during cold winters which are common in many parts of Europe.

It is, therefore a further object of the present invention to provide liquid concentrate compositions containing as active herbicides terbutryne and trifluralin having good emulsifiability, emulsion stability, and low temperature stability under the conditions which they will normally be transported, stored and used.

According to this aspect of the invention, there is provided a herbicidal liquid concentrate composition which does not give crystalline precipitation on standing for 24 hours at $-7°$ C., and which is readily emulsifiable to provide an emulsion which does not give crystalline precipitation with 24 hours from emulsification, comprising:

(a) 7.5 to 18% 2-tert-butylamino-4-ethylamino-6-methylthio-1,3,5-triazine (b) 15 to 25% 2,6-dinitro-N,N-di-n-propyl-4-trifluoromethyl aniline, (c) 28–42% non-phytotoxic alicyclic ketone (d) 5–15% of an emulsifier (e) stabilizing cosolvent selected from one of the following:

(1) 1 to 3% mesityl oxide, or (2) 8 to 15% lower alkyl esters of C-18 unsaturated fatty acids, or (3) a combination of 10 to 20% isophorone and 1 to 3% di-lower alkyl formamide.

The active herbicides may be present in the concentrate composition in the range stated above but preferably in the order of 12 to 16% terbutryne and 18 to 22% trifluralin, most preferably 15% and 20% respectively. All percentages are on a weight basis.

Alicylic ketones which may be used are the cycloalkyl and cycloalkenyl ketones, especially cyclohexanone and cyclohexenone and their lower alkyl derivatives such as 2-methyl-cyclohexanone, 3-methylcyclohexanone, 3-methyl cyclohex-2-en-1-one, 3,5-dimethyl cyclohex-3-en-1-one, 2,6-dimethyl cyclohexanone, 2,2,6-trimethyl cyclohexanone, 3,3,5,5-tetramethyl cyclohexanone and 3,5,5-trimethylcyclohex-2-en-1-one. Cyclohexanone is most preferred.

In addition to special solvents, such liquid concentrate formulations also contain emulsifiers.

The emulsifiers are generally anionic or nonionic emulsifiers, preferably of a mixture of these. Such mixtures are commonly used in the art of pesticide formulation. Examples of suitable anionic emulsifiers are alkali and alkaline earth metal salts of the alkyl and aryl sulfonates, alkyl benzene sulfates and sulfosuccinates such as octyl and nonyl phenyl sulfate, dodecyl benzene sulfonate, isopropyl naphthalene sulfonates, dioctyl and dinonyl esters of sulfosuccinic acids. The preferred anionic emulsifiers are the calcium salts of alkyl benzyl sulfates and sulfonates, most preferably calcium alkyl benzene sulfates.

Examples of suitable non-ionic emulsifiers are fatty acid esters of polyoxyethylene sorbitan, alkylarylpolyethoxy ethanols such as octyl or nonylphenyl polyethoxy ethanol, glyceride esters such as diglyceryl monooleate and ethoxy alkylphenols and cresols such as ethoxylates nonylphenol. The preferred nonionic emulsifiers are the ethoxylated alkylphenols such as ethoxylated nonylphenol.

These emulsifiers are generally mixed in ratios of anionic to non-ionic from 3:7 to 7:3 and preferably about 1:1. The total amount of emulsifier is usually in the order of 5 to 15% of the liquid concentrate on a weight for weight basis. We have found that about 10% of a 1:1 emulsifier blend gives excellent liquid concentrates.

The lower alkyl ester of C-18 unsaturated fatty acid used as cosolvent may be any $C_1$ to $C_4$ alkyl ester of C-18 unsaturated fatty acid such as oleic acid, linoleic acid, tall oil fatty acids just to mention a few. Preferably, the methyl and ethyl esters are contemplated and most preferably methyl oleate.

D-lower alkyl formamides suitable as cosolvents are the $C_1$ to $C_4$ dialkyl formamides, preferably dimethyl and diethyl formamides. Most preferred is dimethyl formamide.

To demonstrate the effect of the inventive combination the following experiments were conducted.

EXAMPLE 1

At Earl Colne, Essex England, fields infested with 228 heads per square meter of blackgrass were sown with winter wheat during the autumn of 1981. The fields were treated preemergence with a 1.5:2 mixture of terbutryne and trifluralin at rates of 1.7 kg/ha and 2.1 kg/ha active ingredients. In both cases, the reduction of heads of blackgrass was 96 percent compared with an untreated field.

EXAMPLE 2

Field tests in winter wheat conducted during the autumn of 1981 at Houghton, Notts England, on plots having a blackgrass infestation of 116 heads per square meter, gave the following results:

| Composition | Terbutryne kg/ha | Trifluralin kg/ha | % Reduction of blackgrass heads | % Damage wheat |
|---|---|---|---|---|
| A | 1.5 | 2.0 | 80 | None |
| B | 1.8 | 2.4 | 81 | None |
| C | 2.0 | 1.0 | 64 | None |
| D | 2.0 | 1.2 | 75 | None |
| E | 2.5 | 1.0 | 80 | None |
| F | 2.5 | 1.2 | 80 | None |
| Chlortoluron (3.6 kg/ha) | — | — | 87 | None |

EXAMPLE 3

Plots of wheat were sown in Cottingham, Lincs England, during the autumn of 1981 and treated preemergence with mixtures of terbutryne and trifluralin. The plots had 267 heads of blackgrass per square meter prior to treatment. The following results were obtained.

| Composition | Terbutryne kg/ha | Trifluralin kg/ha | % Reduction of Blackgrass heads | % Damage of wheat |
|---|---|---|---|---|
| A | 1.5 | 2.0 | 89 | None |
| B | 1.8 | 2.4 | 94 | None |
| C | 2.0 | 1.0 | 72 | None |
| D | 2.0 | 1.2 | 70 | None |
| E | 2.5 | 1.0 | 83 | None |
| F | 2.5 | 1.2 | 91 | None |
| Chlortoluron (3.6 kg/ha) | — | — | 88 | None |

These experiments demonstrate that the mixtures of terbutryne-trifluralin at the ratios used, control blackgrass without adversely affecting the wheat crop.

The mixtures of this invention control weeds by root action and work best under good growing conditions. They will remain active in the soil for several months after application when initial weed control has been successful.

Liquid concentrate compositions of terbutryne and trifluralin were prepared by blending the ingredients outlined in Table 1 in a waring blender after warming to 60° C. All parts are by weight.

TABLE 1

| Compound | Example 4 | Example 5 | Example 6 | Example A | Example B | Example C |
|---|---|---|---|---|---|---|
| Terbutryne | 15 | 15 | 15 | 15 | 15 | 12 |
| Trifluralin | 20 | 20 | 20 | 20 | 20 | 24 |

TABLE 1-continued

| Compound | Example 4 | Example 5 | Example 6 | Example A | Example B | Example C |
|---|---|---|---|---|---|---|
| Cyclohexanone | 32 | 32 | 40 | 49.8 | — | — |
| Isopherone | 15.8 | — | — | — | — | — |
| Methyloleate | — | — | 10 | — | — | — |
| Dimethylformamide | 2 | — | — | — | 49.8 | 12 |
| Mesityloxide | — | 2 | — | — | — | — |
| Xylene | — | — | — | — | — | 37 |
| EL523 + EL524[1] | 15 | 15 | — | 15 | 15 | 15 |
| EMULSOGEN EL + T[2] | — | — | 15 | — | — | — |
| ETHOCELL[3] | 0.2 | 0.2 | 0.2 | 0.2 | 0.2 | — |

[1] Blends of calcium alkylphenol sulfate and nonionic emulsifiers having ⅔ active ingredients and ⅓ inert diluent, product of Atlas Europol.
[2] A 1:1 blend of anionic and nonionic emulsifiers, products of American Hoechst Corp.
[3] Ethoxylated cellulose emulsion stabilizer, a product of Dow Chemicals.

The resulting compositions were tested for emulsifiability by diluting 5 ml of the liquid concentrate with 95 ml water and shaking well.

Low temperature stability was measured by placing samples of the liquid concentrate compositions in a freezer for 24 hours maintained at −7° C. The compositions were then checked to determine whether any crystallization of active ingredients had occured.

Emulsions prepared from liquid concentrate compositions of Table 1 were tested after 24 hours by passing through a 100 mesh sieve to determine of any crystallization had occurred. The results are reported in Table 2.

TABLE 2

| TESTS | Example 4 | Example 5 | Example 6 | Example A | Example B | Example C |
|---|---|---|---|---|---|---|
| (1) Emulsifiability | Good | Good | Good | Good | Good | Good |
| (2) Low temp. stability at −7° C. | Good | Good | Good | Poor (a) | Good | Poor (a) |
| (3) Emulsion Stability 24 hours | Good | Good | Good | Poor (b) | Poor (b) | Poor (b) |

(a) terbutryne crystals precipitated
(b) trifluralin and terbutryne crystals precipitated From Tables 1 and 2, it is evident that only Examples 4, 5 and 6 of this invention retained emulsion stability and low temperature stability compared to similar compositions specifically taught in the prior art or obvious therefrom.

Some of the weeds controlled by the inventive method are:

| | |
|---|---|
| Annual meadow grass | Poa annua |
| Rough meadow grass | Poa trivialis |
| Black bindweed | Polygonum convolulus |
| Charlock | Sinapis arvensis |
| Common chickweed | Stellaria media |
| Common Field-speedwell | Veronica agrestis |
| Common Fumitory | Fumaria officinalis |
| Common Mouse-ear | Cerastium aryense |
| Common Orache | Atriplex patula |
| Common Poppy | Papaver spp. |
| Corn Chamomile | Anthemis Arvensis |
| Fat Hen | Chenepodium album |
| Fool's Parsley | Aethusa Cynapium |
| Groundsel | Senecio vulgaris |
| Henbit dead-nettle | Lamium amplexicaule |
| Ivy-leaved Speedwell | Veronica Heteraefolia |
| Parsley Piert | Aphanes arvensis |
| Pinappleweed | Matricaria matricariodes |
| Red Dead-nettle | Lamium purpureum |
| Redshank | Polygonum persicaria |
| Scentless Mayweed | Matricaria maritimum |
| Shepherd's Purse | Capsella bursa-pastoris |
| Annual Nettle | Urtica urens |
| Wild Radish | Raphanus raphanistrum |
| Venus's-looking-glass | Specularia perfoliata |
| Blackgrass | Alopecurus myosuoides |
| Cleavers | Galium aparine |
| Flaxweed | Linum |
| Knotweed | Polygonum aviculare |

We claim:

1. A method for obtaining satisfactory blackgrass control in cereal crops, without injury to the cereal crops, comprising preemergent application of a mixture consisting essentially of terbutryne and trifluralin having a ratio of 1:2 to 2.5:1 in sufficient amount to control the blackgrass and yet not injure the crops at a rate of application of the mixture from 1.0 to 4.5 kilogram per hectar.

2. A method in accordance with claim 1, wherein the ratio of terbutryne to trifluralin is from 1.2:2 to 1:1.

3. A method in accordance with claim 1, wherein the rate of application is 1.5 to 3.5 kg/ha.

4. A method in accordance with claim 1 wherein the cereal crops are winter cereals.

5. A method in accordance with claim 4, wherein the cereal crop is winter wheat or winter barley.

6. A method in accordance with claim 1 wherein the blackgrass population is greater than 60 heads per sq. meter.

7. A method in accordance with claim 1 wherein the ratio of terbutryne to trifluralin in the mixture is substantially 1.5:2.0 and the rate of application is between 1.75 to 3.5 kg/ha.

8. A method for obtaining satisfactory blackgrass control in a winter wheat crop without injury to the winter wheat crop and in which the blackgrass population is greater than 60 heads per square meter which comprises the preemergent application of a mixture consisting essentially of terbutryne and trifluralin in a ratio of 1:2 to 2.5:1 at a rate of application of 1.0 to 4.5 kilograms per hectar.

9. The method of claim 8 wherein the ratio of turbutryn to trifluralin is from 1.2:2 to 1:1 and the rate of application is 1.5 to 3.5 kg/ha.

10. A method in accordance with claim 8, wherein the ratio of turbutryn to trifluralin in the mixture is substantially 1.5:2 and the rate of application is between 1.75 and 3.5 kg/ha.

* * * * *